(12) United States Patent
Vyklicky et al.

(10) Patent No.: US 9,981,965 B2
(45) Date of Patent: May 29, 2018

(54) PROCESS FOR PREPARING IDELALISIB

(71) Applicant: SYNTHON B.V., Nijmegen (NL)

(72) Inventors: Libor Vyklicky, Blansko (CZ); Miroslav Zabadal, Blansko (CZ)

(73) Assignee: Synthon B.V., Nijmegen (NL)

( * ) Notice: Subject to any disclaimer, the term of this patent is extended or adjusted under 35 U.S.C. 154(b) by 0 days. days.

(21) Appl. No.: 15/563,254

(22) PCT Filed: Mar. 24, 2016

(86) PCT No.: PCT/EP2016/056628
§ 371 (c)(1),
(2) Date: Sep. 29, 2017

(87) PCT Pub. No.: WO2016/156240
PCT Pub. Date: Oct. 6, 2016

(65) Prior Publication Data
US 2018/0093987 A1 Apr. 5, 2018

(30) Foreign Application Priority Data
Mar. 31, 2015 (WO) .................. PCT/EP2015/057007

(51) Int. Cl.
*C07D 239/91* (2006.01)
*C07D 473/34* (2006.01)
*B01D 9/00* (2006.01)
*C07B 63/02* (2006.01)

(52) U.S. Cl.
CPC ........... *C07D 473/34* (2013.01); *B01D 9/005* (2013.01); *C07B 63/02* (2013.01); *C07D 239/91* (2013.01)

(58) Field of Classification Search
CPC ............................. C07D 239/91; C07D 473/34
See application file for complete search history.

(56) References Cited

U.S. PATENT DOCUMENTS 7,932,260 B2 * 4/2011 Fowler ................ C07D 473/16
514/266.1

* cited by examiner

*Primary Examiner* — Bruck Kifle
(74) *Attorney, Agent, or Firm* — Buscher Patent PLLC

(57) ABSTRACT

The present invention relates to an improved process for preparing Idelalisib (1). In this process, acid addition salts of idelalisamine (2) are useful intermediates for purification purposes.

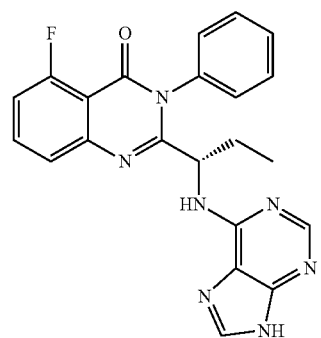

(1)

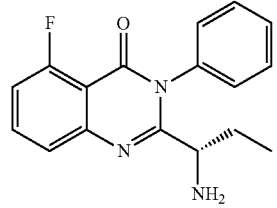

(2)

17 Claims, No Drawings

PROCESS FOR PREPARING IDELALISIB

BACKGROUND OF THE PRESENT INVENTION

This invention relates to the preparation of pharmaceuticals and their intermediates. In particular it relates to an improved process of preparing idelalisib (1). The process runs via acid addition salts of idelalisamine (2). Idelalisamine (2) is a late stage intermediate in the process for preparing idelalisib (1). The acid addition salts of idelalisamine can be purified easily via precipitation/crystallization and provide an easy purification option for a late stage intermediate in the process for preparing idelalisib (1).

BRIEF DESCRIPTION OF THE PRESENT INVENTION

Idelalisib (WO2005113556) is a PI3Kδ inhibitor of structure (1) and is used for the treatment of patients with follicular lymphoma, relapsed small lymphocytic lymphoma and relapsed chronic lymphocytic leukaemia.

WO2005113556 describes the preparation of idelalisib as depicted below.

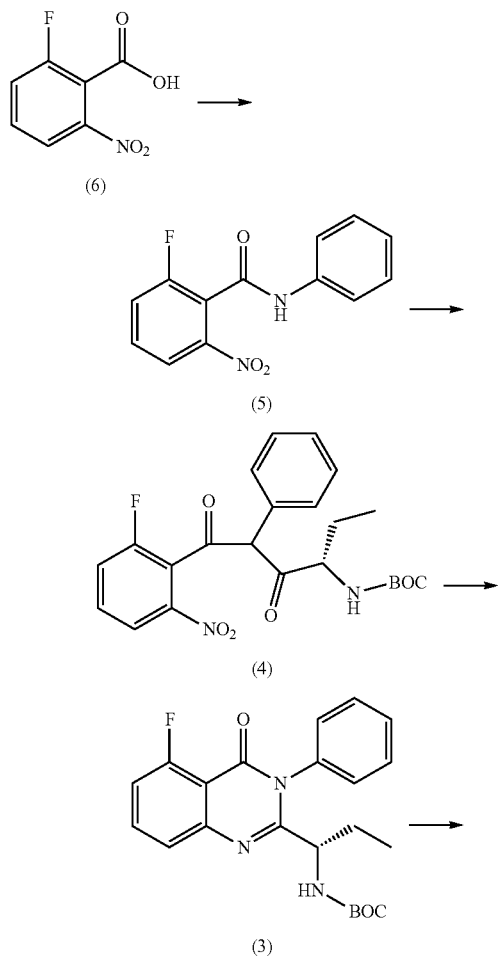

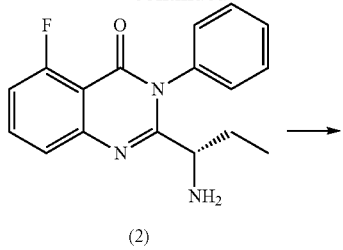

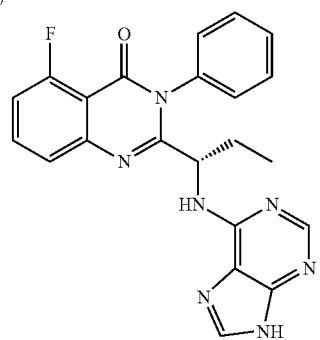

The process for preparing idelalisib as described in WO2005113556 requires chromatographic purification steps for intermediates (4) and (3), and for idelalisib (1).

Chromatographic purification steps are tedious and expensive process steps on an industrial scale. Therefore, there is a need for alternative methods which reduce the number of chromatographic purification steps in the preparation of idelalisib.

SUMMARY OF THE INVENTION

The present invention relates to improvement of the overall efficiency in the process for preparing idelalisib (1) and to the acid addition salts of idelalisamine (2).

DETAILED DESCRIPTION OF THE INVENTION

Treatment of idelalisamine (2) with several acids, results in isolation of the corresponding idelalisamine acid addition salt in high yield and purity. Also when crude intermediate (3) was used as starting material for preparing idelalisamine, the acid addition salt of idelalisamine was isolated in a yield and purity comparable with the original procedure of WO2005113556. This precipitation and/or crystallisation of an acid addition salt of idelalisamine obviates earlier chromatographic steps in the synthesis, thereby making the process more efficient and less costly. The acid addition salt of idelalisamine can be used as such in the final step for preparing idelalisib (1).

In a first aspect the invention relates to processes for preparing idelalisib (1) that have acid addition salts of idelalisamine (2) as intermediate.

Several acids were tested for their capability to form acid addition salts with idelalisamine (2) and for their usefulness in the purification of idelalisamine. Some of the tested acids were found to produce acid addition salts of idelalisamine that are easy to precipitate or crystallise, while others formed only oils, very fine suspensions, or material that liquefied during filtration.

Best results were achieved using hydrochloric acid, benzoic acid, oxalic acid, malonic acid, fumaric acid, tartaric acid, ethanesulphonic acid, or p-toluenesulphonic acid and the acid addition salts of these acids are the preferred salts of the current invention. Of these, the acid addition salt of hydrochloric acid is the most preferred. The hydrochloric acid salt produces a crystalline material from several solvents such as 1,4-dioxane, EtOAc, THF, 2-Me-THF, $CHCl_3$, $CH_2Cl_2$, Toluene and t-BuOH, which are the preferred solvents in this invention. Most preferred solvent is 2-Me-THF.

The results of the tests are summarized in the table below.

| Acid | 1,4-Dioxane | EtOAc | THF | 2-Me-THF | $CHCl_3$ |
|---|---|---|---|---|---|
| HCl | 85% | 92% | 92% | 100% | 30.4% |
| $H_2SO_4$ | | | No | 76.9% (oil) | |
| $HNO_3$ | | | No | | |
| $H_3PO_4$ * | | | 17.3% (oil) | 17% (oil) | |
| Formic acid | | | Traces | | |
| Acetic acid | no | | No | No | No |
| Benzoic acid | | | No | 31.6% | |
| Oxalic acid | 2.9% | | 48% | 86.5% | 81.1% |
| Malonic acid | | | | 79.3% | |
| Fumaric acid | | | 79% | | |
| Maleic acid | | | No | (oil) | |
| Tartaric acid | | | | 36.5% | |
| $EtSO_3H$ | | 106 ** | 97% | | Traces (oil) |
| p-TosOH | | No | No | 93.6% | |

* 0.66 equivalents used
** sticky white crystals (oil) suspension/colloid/liquefied during isolation Should the precipitation of the acid addition salt of idelalisamine (2) not lead to material of sufficient quality, the acid addition salt can be recrystallized by methods generally known in the art. Typical examples of such methods include: allowing a warm solution of the salt to cool down; allow the solvent of a solution of the salt to slowly evaporate, and; addition of an anti-solvent to a solution of the salt.

In a second aspect the invention relates to acid addition salts of idelalisamine (2). Preferred acid addition salts of idelalisamine (2) are the salts of hydrochloric acid, benzoic acid, oxalic acid, malonic acid, fumaric acid, tartaric acid, ethanesulphonic acid, or p-toluenesulphonic acid. Most preferred salt is the hydrochloride salt.

The salts of this invention can be used as late starting material for preparing idelalisib (1). Adjustments to the process as described in WO2005113556 to compensate for the use of the salts as starting material instead of the free base are routine to the person skilled in the art.

The new salts allow substituting one or more of the chromatographic purification steps in the process of WO2005113556 with purification by precipitation and/or crystallisation in the idelalisamine stage. Therewith making the process of preparing idelalisib (1) more efficient on industrial scale from a time and cost perspective.

The invention will be further illustrated by the following, non-limiting, examples.

EXAMPLES

Example 1

Preparation of HCl Salts of Idelalisamine (2) in Various Solvents 0.12 gram (0.357 mmol) of idelalisamine with 88% purity was dissolved in 3 ml of solvent. 0.032 ml of hydrochloric acid (37%, 0.357 mmol) was added. The mixture was heated to 90° C. (70° C. for ethylacetate, 35° C. for CH2Cl2) and allowed to cool down to 0° C. (20° C. for 1,4-dioxane).

| Solvent | Yield | Purity |
|---|---|---|
| Ethylacetate | 0.110 g (90%) | 97.6% |
| Butane-2-ol | 0.074 g (62.1%) | |
| Toluene | 0.062 g (52.0%) | |
| 1,4-dioxane | 0.101 g (83%) | 98.5% |
| THF | 0.110 g (91%) | 98.8% |
| 2-Me-THF | 0.122 g (102%) | |
| $CH_2Cl_2$ | 0.097 g (79%) | 97.2% |

Example 2

Preparation of Salts of Idelalisamine (2) with Various Acids in THF 0.12 gram (0.357 mmol) of idelalisamine with 88% purity was dissolved in 3 ml of THF. 0.357 mmol of acid was added. The mixture was heated to 60° C. and allowed to cool down to 0° C.

| Acid | Yield |
|---|---|
| Ethanesulphonic acid | 0.141 g (97%) |
| Fumaric acid | 0.117 g (79%) |
| Sulphuric acid | — |
| Acetic acid | — |
| Benzoic acid | Precipitates at 0° C., dissolves at 15° C. |
| Nitric acid | — |
| P-toluenesulphonic acid | — |
| Phosphoric acid | 0.016 g (11.4%), liquefies during filtration |
| Oxalic acid | 0.066 g (48%) |
| Maleic acid | — |
| Hydrochloric acid | 0.106 g (89%) |

Example 3

Preparation of Salts of Idelalisamine (2) with Various Acids in 2 Me THF 0.12 gram (0.357 mmol) of idelalisamine with 88% purity was dissolved in 3 ml of 2-Me-THF. 0.357 mmol of acid was added. The mixture was heated to 60° C. and allowed to cool down to 0° C.

| Acid | Yield |
|---|---|
| Sulphuric acid | 0.108 g (77%), liquefies during filtration |
| Acetic acid | — |
| Benzoic acid | 0.047 g (31.5%) |
| P-toluenesulphonic acid | 0.156 g (94%) |
| Phosphoric acid | 0.016 g (11.4%), liquefies during filtration |
| Oxalic acid | 0.119 g (86%) |
| Maleic acid | oil |
| Malonic acid | 0.113 g (79%) |
| (2R,3R)-tartaric acid | 0.058 g (36.5%) |

Example 4

Preparation of Salts of Idelalisamine (2) with Various Acids in 1,4-dioxane 0.12 gram (0.357 mmol) of idelalisamine with 88% purity was dissolved in 3 ml of 1,4-dioxane. 0.357 mmol of acid was added. The mixture was heated to 90° C. and allowed to cool down to 20° C.

| Acid | Yield |
|---|---|
| Oxalic acid | 0.004 g (3.49%) |
| Acetic acid | — |

Example 5

Preparation of Salts of Idelalisamine (2) with Various Acids in Chloroform 0.12 gram (0.357 mmol) of idelalisamine with 88% purity was dissolved in 3 ml of 2 Me THF. 0.357 mmol of acid was added. The mixture was heated to 55° C. and allowed to cool down to 0° C.

| Acid | Yield |
|---|---|
| Hydrochloric acid | 0.030 g (30.4%) |
| Acetic cid | — |
| Ethanesulphonic acid | Liquefies during filtration |
| Oxalic acid | 0.093 g (66.9%) |

Example 6

Purification of Idelalisamine (2) Via Hydrochloric Acid Extraction 0.442 g (1.383 mmol) of idelalisamine with 93% purity was dissolved in 10 ml of dichloromethane and extracted with 19 ml of 2% HCl. After separating the layers, the organic phase was extracted with 6 ml of 1.5% HCl.

A solution of 50% NaOH was added to the combined aqueous phases until a pH of approximately 10 was reached. A white precipitate is formed which is filtered and washed with 5 ml of water. The product was dried in a vacuum oven at 40° C. under a pressure of 100 torr with nitrogen stripping for 5 hours.

Yield: 0.321 g (77%) of white crystals with a purity of 98%.

Example 7

Preparation of tert-butyl (S)-(1-(5-fluoro-4-oxo-3-phenyl-3,4-dihydroquinazolin-2-yl)propyl)carbamate (3)

6.41 g, (14.39 mmol) of compound (4) was dissolved in 55 ml acetic acid at room temperature. Zinc dust (5.65 g, 86 mmol) was added in small portions. After each addition, a rise in internal temperature was observed. The reaction mixture was allowed to cool below 35° C. before the next portion was added. Addition took ca. 30 min.

After 3 hours the reaction mixture was filtered through celite, the filter cake was washed with a small amount of acetic acid and the filtrate was concentrated in vacuo.

The resulting oil was split in ca 7:3 ratio, the smaller portion was kept for future experiments and the larger portion was diluted with approximately 20 ml of $CH_2Cl_2$. The $CH_2Cl_2$ solution was filtered through celite to remove solid material present in the solution and purified by chromatography using MPLC.

2.22 g (5.59 mmol, 55.5%) of compound (3) was isolated.

Example 8

Preparation of Idelalisamine (2) Starting from Purified (3)

2.22 g (5.59 mmol) of compound (3) isolated after column chromatography as described in example 7 was dissolved in 6 ml of $CH_2Cl_2$. 3.82 g (33.5 mmol) of trifluoroacetic acid (TFA) was added and the reaction mixture was stirred at room temperature for 5 hours. The reaction mixture was concentrated in vacuo and partitioned between 10 ml of $CH_2Cl_2$ and 60 ml of 10% $K_2CO_3$. The aqueous layer was extracted with additional $CH_2Cl_2$ and the combined organic layers were washed with water and brine, dried over $MgSO_4$, filtered, concentrated and dried in vacuo for 2 hours to result in 1.49 g (5.01 mmol, 89.7%) of idelalisamine (2) with a purity of 93%.

Yield starting from compound (4) following examples 7 and 8: 49.7%

Example 9

Preparation of Idelalisamine.HCl (2).HCl Starting from Crude (3)

The 0.3 fraction of crude (3) (2.5 g) that was set aside in example 7 was dissolved in 10 ml of $CH_2Cl_2$, filtered over celite and evaporated to dryness to yield 2 gram of an oil.

1 gram of this oil was dissolved in 3 ml of $CH_2Cl_2$. 0.8 g (7.1 mmol) of trifluoroacetic acid (TFA) was added and the reaction mixture was stirred at room temperature for 3 hours.

The reaction mixture was concentrated in vacuo and partitioned between 5 ml of $CH_2Cl_2$ and 20 ml of saturated $NaHCO_3$. The aqueous layer was extracted with additional $CH_2Cl_2$ and the combined organic layers were washed with water and brine, dried over $MgSO_4$, filtered, concentrated and dried in vacuo for 30 min to result in 0.576 g (1.124 mmol, 95%) of crude idelalisamine (2).

This crude material was dissolved in 5 ml of 2-Me-THF and 0.175 ml (2 mmol) of 35% HCl was added. The mixture was stirred at 0° C. for 15 min. and filtered. The residue was washed with 2-Me-THF and dried in vacuo at 40° C. overnight to result in 0.369 g of idelalisamine.HCl (2).HCl with a purity of 98.4% and a total assay of 79.7%.

Yield starting from compound (4) following examples 7 and 9: 51.4%.

The invention claimed is:
1. In a process for synthesizing idelalisib of formula (1) from idelalisamine of formula (2),

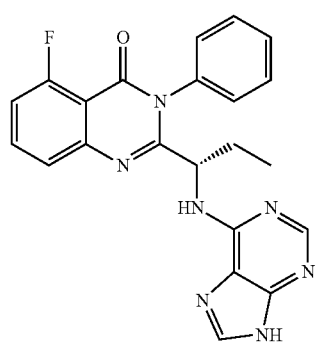

(1)

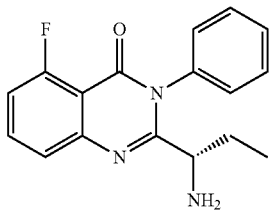

(2)

the improvement for which comprises isolating an acid addition salt of idelalisamine before its chemical conversion to idelalisib.

2. The process of claim 1, wherein the acid in the acid addition salt of idelalisamine (2) is hydrochloric acid, benzoic acid, fumaric acid, malonic acid, tartaric acid, ethanesulphonic acid, p-toluenesulphonic acid or oxalic acid.

3. The process of claim 1, wherein the acid in the addition salt of idelalisamine is hydrochloric acid.

4. A process which comprises:
(a) mixing idelalisamine free base of formula 2

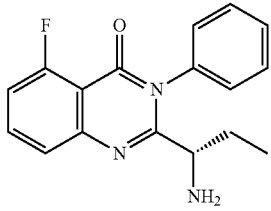

(2)

with an acid selected from hydrochloric acid, benzoic acid, fumaric acid, malonic acid, tartaric acid, ethanesulphonic acid, p-toluenesulphonic acid or oxalic acid, in a solvent or solvent mixture and
(b) isolating the idelalisamine acid addition salt.

5. A process of claim 4, wherein the mixing of idelalisamine free base with an appropriate acid of step (a) is performed in a crude reaction mixture.

6. A process according to claim 5, wherein step (a) is performed in a solvent or solvent mixture comprising at least one of: 1,4-dioxane, EtOAc, THF, 2-Me-THF, $CHCl_3$, $CH_2Cl_2$, Toluene and t-BuOH.

7. A process according to claim 4, wherein step (a) is performed in 2-Me-THF or a solvent mixture comprising 2-Me-THF.

8. A process according to claim 4, wherein step (b) is performed by crystallising the idelalisamine acid addition salt.

9. A process according to claim 4, which further comprises purifying said isolated idelalisamine acid addition salt which comprises the steps of:
(i) dissolving the salt in a solvent, and
(ii) inducing crystallisation of the idelalisamine acid addition salt.

10. The process of claim 9 wherein the solvent in step (i) is chosen from 1,4-dioxane, EtOAc, THF, 2-Me-THF, $CHCl_3$, $CH_2Cl_2$, Toluene and t-BuOH.

11. The process of claim 9 wherein the solvent in step (i) is 2-Me-THF.

12. An acid addition salt of idelalisamine of formula (2)

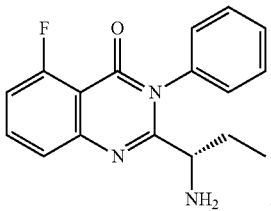

(2)

13. The acid addition salt of claim 12, wherein the acid in the acid addition salt is hydrochloric acid, benzoic acid, fumaric acid, malonic acid, tartaric acid, ethanesulphonic acid, p-toluenesulphonic acid or oxalic acid.

14. An acid addition salt of claim 12, wherein the acid in the acid addition salt is hydrochloric acid.

15. The process according to claim 1 in which the improvement further comprises purifying said isolated idelalisamine acid addition salt which comprises the steps of:
(i) dissolving the salt in a solvent, and
(ii) inducing crystallisation of the idelalisamine acid addition salt.

16. The process according to claim 15, wherein the acid in the addition salt of idelalisamine is hydrochloric acid.

17. The process according to claim 16, wherein said solvent in step (i) is 2-Me-THF.

* * * * *